United States Patent [19]

Zaugg et al.

[11] 4,025,512
[45] May 24, 1977

[54] 6a-AZACANNABINOIDS

[75] Inventors: Harold Elmer Zaugg, Lake Forest; David Lloyd Arendsen, Libertyville, both of Ill.

[73] Assignee: Abbott Laboratories, North Chicago, Ill.

[22] Filed: Apr. 14, 1976

[21] Appl. No.: 676,779

[52] U.S. Cl. .................... 260/244 R; 424/248.54
[51] Int. Cl.² ............ C07D 265/00; C07D 273/00; C07D 295/00
[58] Field of Search .................... 260/244; 424/248

[56] References Cited

UNITED STATES PATENTS 3,122,538  2/1964  Clauson-Kaas et al. ....... 260/244 R
3,905,956  9/1975  Derieg et al. ....... 260/244

OTHER PUBLICATIONS

Chem. Abst. 76, 25207e, (1972); Ben–Ishai et al.

*Primary Examiner*—Albert T. Meyers
*Assistant Examiner*—D. W. Robinson
*Attorney, Agent, or Firm*—Vincent A. Mallare; Robert L. Niblack

[57] ABSTRACT

A compound of the formula

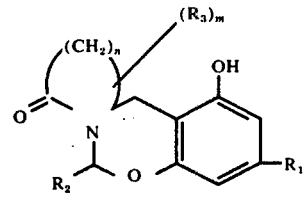

wherein $n = 2$ or $3$; $R_1$ is a $C_3$–$C_{20}$ alkyl or arylalkyl; $R_2$ is loweralkyl or phenyl; and $R_3$ is H or replaces the hydrogens in $(CH_2)_n$ with $CH_3$; and $m$ is 1, 2 or 4.

These compounds exhibit central nervous system activity and are useful as antidepressants.

13 Claims, No Drawings

6a-AZACANNABINOIDS

SUMMARY OF THE INVENTION

The present invention is related to cannabinoid analogs containing a bridgehead nitrogen and more particularly to 6a-azacannabinoids which are useful as antidepressants and exhibit central nervous system activity in warm-blooded animals.

By using the α-amidoalkylation reaction of 2-ethoxylactams with 5-substituted resorcinols, followed by cyclization with an aldehyde, the first examples of cannabinoid analogs containing a bridgehead nitrogen were prepared.

DETAILED DESCRIPTION OF THE INVENTION

This invention relates to 6a-azacannabinoids which are useful as antidepressants. The azacannabinoids are compounds falling within the following structural formula:

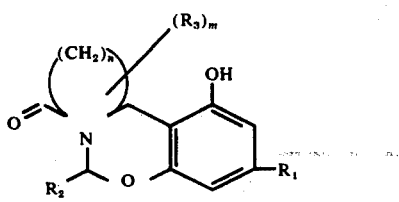

wherein $n = 2$ or $3$; $R_1$ is a $C_3$–$C_{20}$ alkyl or arylalkyl; $R_2$ is a loweralkyl or phenyl; and $R_3$ is H or replaces the hydrogens in $CH_2)_n$ with ; and $CH_3$, and $m$ is 1, 2 or 4.

The term "$C_3$–$C_{20}$ alkyl" as used herein, refers to both straight and branched chain alkyl radicals including n-propyl, iso-propyl, n-butyl, sec-butyl, tertiary-butyl, n-pentyl, n-hexyl, 2-heptyl, n-heptyl, 3-methyl-2-octyl, n-octyl, n-nonyl, 2-tetradecyl, 2-eicosanyl, and the like.

The term "arylalkyl" refers to an alkyl group of 1 to 10 carbon atoms where one of the hydrogen atoms of the alkyl group is substituted by phenyl or a substituted phenyl.

The term "loweralkyl" refers to a $C_1$ to $C_6$ alkyl groups including methyl ethyl, n-propyl, iso-propyl, n-butyl, sec-butyl, tertiary-butyl, n-pentyl, iso-pentyl, neo-pentyl, n-hexyl and the like.

The compounds of this invention exhibit central nervous system activity, particularly as an antidepressant of the central nervous system in warmblooded animals. The antidepressant activity is obtained at dosages of from 10 to 40 mg./kg. of body weight orally and from 10 to 20 mg./kg. body weight interperitoneally (i.p.).

The compounds of the present invention may be prepared by means of a variety of techniques. For example, the 5-membered ring compounds or homologs can generally be prepared by the α-amidoalkylation of 5-(3-methyl-2-octyl)-resorcinol (2) by 5-ethoxy-2-pyrrolidinone (5) which can be prepared by borohydride reduction of succinimide as described in the publication of J. C. Hubert, et al, *Tetrahedron*, volume 31, p. 1437 (1975). Then in two steps, the mono-azacannabinoid (7) as shown in the flow diagram below, is produced.

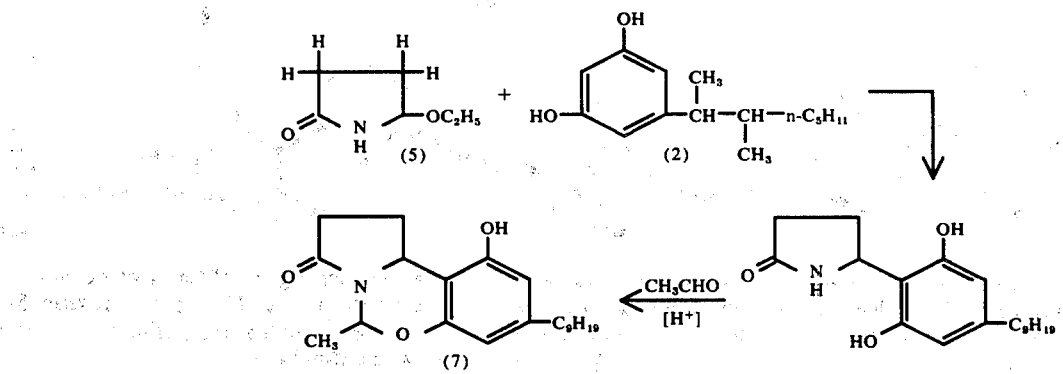

Similarly, the α-amidoalkylation of 5-(3-methyl-2-octyl)-resorcinol (2) by tetramethylpyrrolidinone (6) leads to the corresponding tricyclic compound (8) as shown below in the flow diagram:

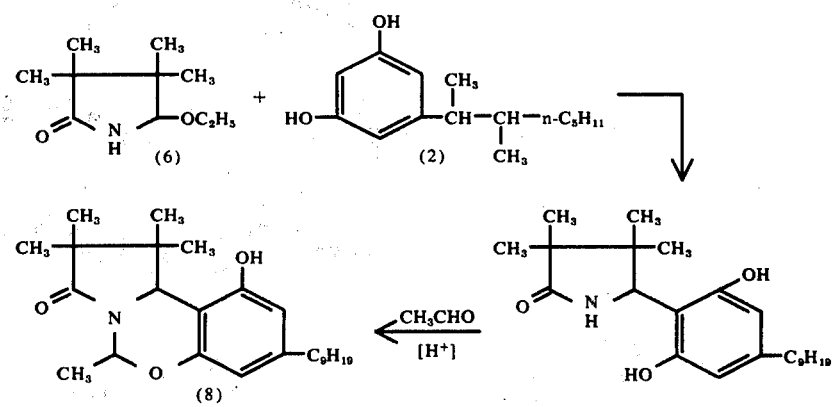

In the synthesis or preparation of the 6-membered ring homologues, such as compound (11) shown below in the flow diagram, this is synthesized generally by using the ethoxypiperidone (9). In the general synthesis, the ethoxypiperidone (9) is condensed with 5-(3-methyl-2-octyl)-resorcinol(2) to give compound (11).

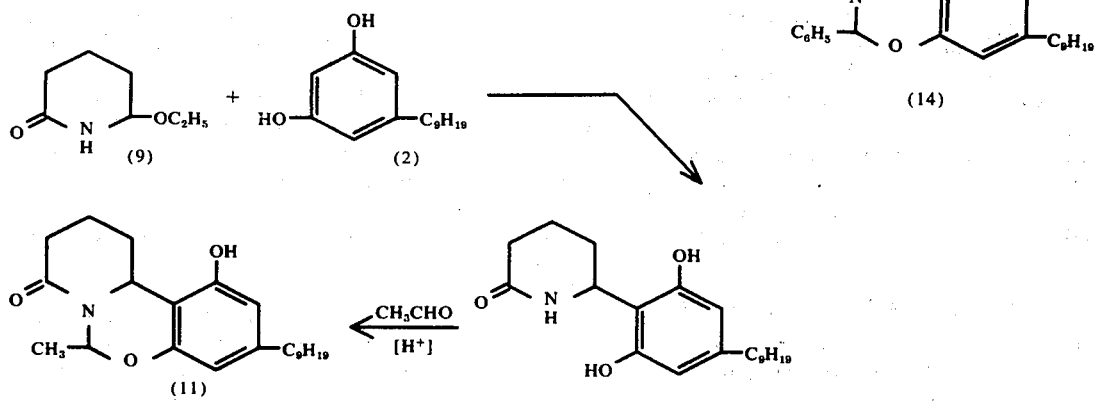

In a similar manner, to produce the compound (12), the arylalkyl resorcinol (10) is used as shown below in the flow diagram.

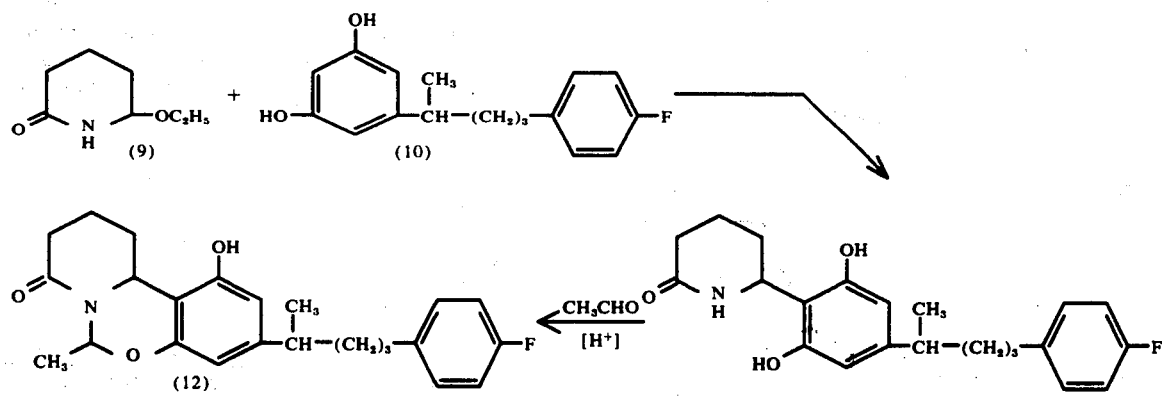

Additional structural variations may be obtained by utilizing n-butyraldehyde and benzaldehyde in the second step to produce compounds (13) and (14) respectively.

In the analog to Δ⁹-tetrahydrocannabinoids, the 9-methyl derivative (17) is prepared from 5-(3-methyl-2-octyl)-resorcinols and piperidone (15) as shown in the flow diagram below:

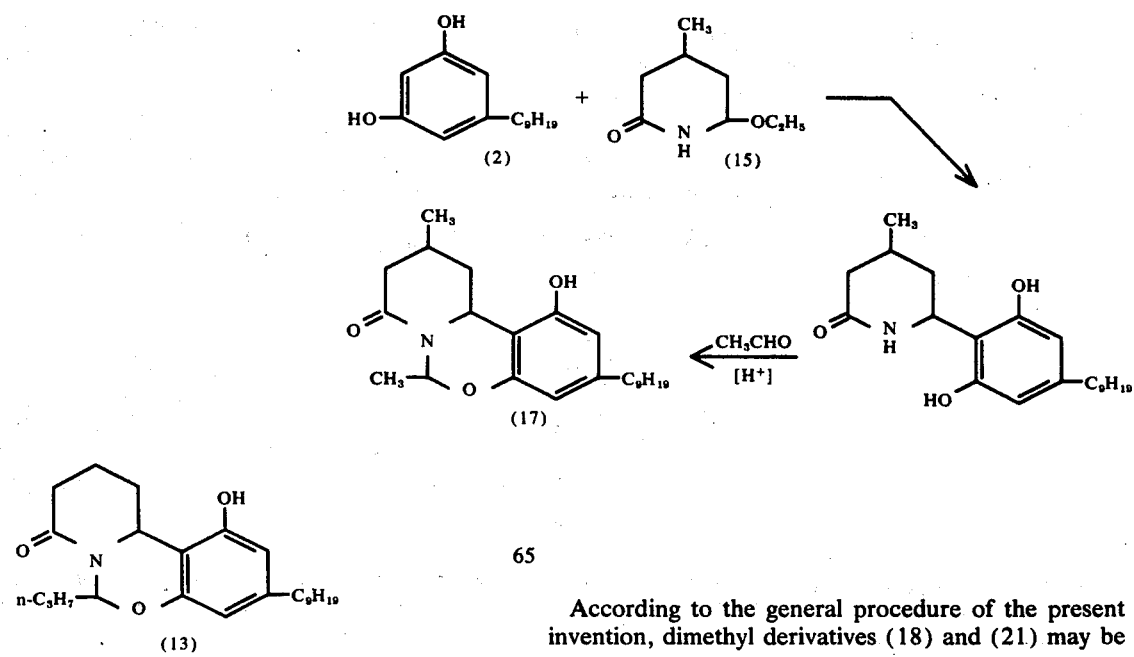

According to the general procedure of the present invention, dimethyl derivatives (18) and (21) may be synthesized as illustrated in the flow diagrams below. In each case, the intermediate resorcinol corresponds to the desired compound or derivative being synthesized.

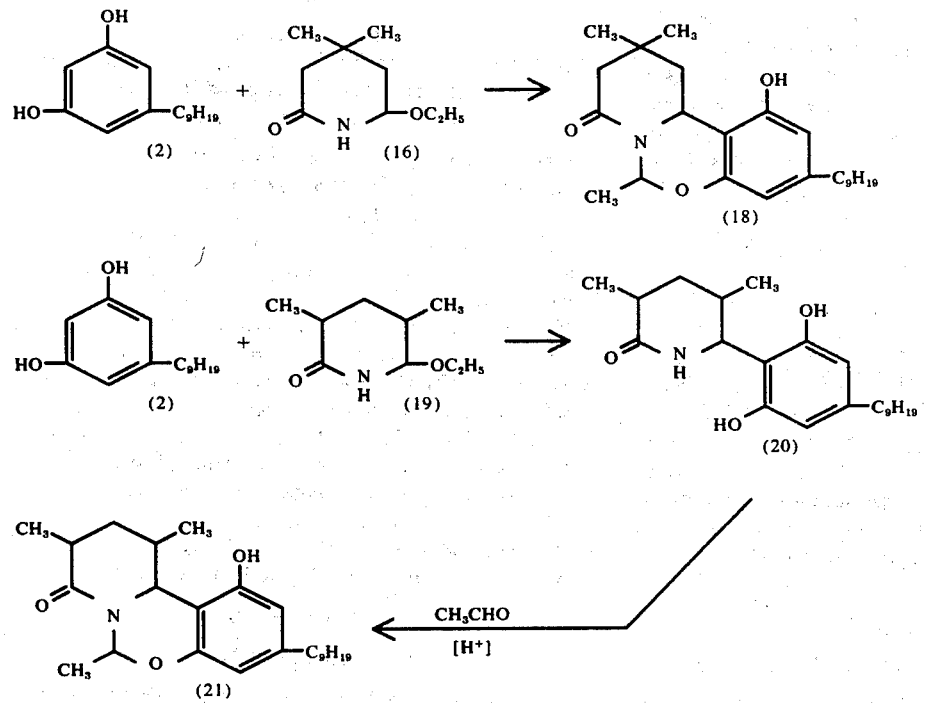

The following examples further illustrate the present invention.

EXAMPLE 1

Preparation of
11-Hydroxy-6-methyl-9-(3-methyl-2-octyl)-1,2,3,12-tetrahydro-4H,6H-pyrido[1,2-c] [1,3]benzoxazine 4-one (11)

A solution of 14.2 g. (0.06 mole) of the resorcinol (2) and 11.5 g. (0.08 mole) of 6-ethoxy-2-piperidone (9) in 75 ml. of saturated ethanolic hydrogen chloride was stirred at room temperature for 24 hours. It was then worked up to give 26.3 g. of a glassy product which could be used in the next step, or purified by column-chromatography on Florisil using 2% methanol in chloroform for elution.

A solution of 7.4 g. (0.022 mole) of this crude resorcinol derivative in 40 ml. of acetaldehyde was then treated with 1 ml. of 6N hydrochloric acid and stirred at room temperature for 2.5 hours. It was poured into water and worked up. However, the glassy product (6 g.) obtained from the chloroform extract, partially crystallized (2.1 g., m.p. 227°–229°) on treatment with acetonitrile. The remainder was chromatographed on Florisil (2% methanol in benzene) to give an additional 2.8 g., m.p. 229°–230° (total yield: 4.9 g., 62%). Recrystallization from ethanol gave a pure product (11), m.p. 230°–232°. The IR and PMR spectra were consistent with the structure of the compound (11).

Analysis Calcd. for: $C_{22}H_{33}NO_3$: C, 73.50; H, 9.25; N, 3.90 Found: C, 73.70; H, 9.55; N, 3.72

EXAMPLE 2

Preparation of
11-Hydroxy-9-(3-methyl-2-octyl)-6-n-propyl-1,2,3,12-tetrahydro-4H,6H-pyrido[1,2-c] [1,3]benzoxazine-4-one (13)

By using n-butyraldehyde in place of acetaldehyde in the procedure described in Example 1, above, there was obtained a 24% yield of the title compound, m.p. 205°–206°.

Analysis Calcd. for: $C_{24}H_{37}NO_3$: C, 74.39; H, 9.63; N, 3.61 Found: C, 74.75; H, 9.85; N, 3.60

EXAMPLE 3

Preparation of
11-Hydroxy-9-(3-methyl-2-octyl)-6-phenyl-1,2,3,12-tetrahydro-4H,6H-pyrido [1,2-c] [1,3]benzoxazine-4-one (14)

In a manner similar to the procedure described in Example 1, benzaldehyde was substituted for the acetaldehyde. As a result, there was obtained a 22% yield of the title compound, m.p. 231°–232°.

Analysis Calcd. for: $C_{27}H_{35}NO_3$: C, 76.94; H, 8.37; N, 3.32 Found: C, 76.56; H, 8.55; N, 3.20

EXAMPLE 4

Preparation of
9-(4-p-Fluorophenyl-2-pentyl)-11-hydroxy-6-methyl-1,2,3,12-tetrahydro-4H,6H-pyrido[1,2-c] [1,3]benzoxazine-4-one (12)

In a preparation as described in Example 1, above, the piperidone (9) with 5-(4-p-fluorophenyl-2-pentyl)-resorcinol (10) produced a glassy product which was treated with acetaldehyde to produce a 26% yield of (12), m.p. 204°–205°.

Analysis Calcd. for: $C_{24}H_{28}FNO_3$: C, 72.52; H, 7.10; N, 3.52 Found: C, 72.48; H, 7.23; N, 3.47

EXAMPLE 5

Preparation of 10-Hydroxy-5-methyl-8-(3-methyl-2-octyl)-1,2,3,11-tetrahydro-5H-pyrrolo[1,2-c][1,3]benzoxazine 3-one (7)

A solution of 18.9 g. (0.08 mole) of the resorcinol (2) and 11.6 g. (0.089 mole) of 5-ethoxy-2-pyrrolidinone (5) in 90 ml. of saturated ethanolic hydrogen chloride was stirred at room temperature for one week. After this period, there was produced 22.0 g. of amorphous product which, on treatment with acetaldehyde, was converted to a 38% yield of compound (7), m.p. 176°–177°.

Analysis Calcd. for: $C_{21}H_{31}NO_3$: C, 73.01; H, 9.04; N, 4.05 Found: C, 72.83; H, 9.15; N, 4.05

EXAMPLE 6

Preparation of 5-Ethoxy-3,3,4,4-tetramethyl-2-pyrrolidinone (6)

By the method described in the publication of Speckamp et al., *Tetrahedron*, 31, p. 1437 (1975), the corresponding cyclic imide was reduced by sodium borohydride in ethanol followed by the addition of a suitable acid. Thus, from 2,2,3,3-tetramethylsuccinimide, there was obtained a 93% yield of compound (6), m.p. 110°–111°.

EXAMPLE 7

Preparation of Ethoxylactams (15) and (16)

In a manner similar to that described in Example 6, above, from 3-methylglutarimide there was obtained an 81% yield of compound (15), 6-ethoxy-4-methyl-2-piperidinone, which was a waxy solid contaminated by almost an equal amount (pmr) of the corresponding hydroxylactam. By a similar reduction of 3,3-dimethylglutarimide there was produced a 95% yield of compound (16), 4,4-dimethyl-6-ethoxy-2-piperidone, m.p. 105°–115°.

EXAMPLE 8

Preparation of Methyl Derivatives of Compounds (7) and (11):
10-Hydroxy-8-(3-methyl-2-octyl)-1,1,2,3,5-pentamethyl-1,2,3,4-tetrahydro-5H-pyrrolo[1,2-c][1,3]benzoxazine-3-one (8);
2,6-Dimethyl-11-hydroxy-9-(3-methyl-2-octyl)-1,2,3,12-tetrahydro-4H,6H-pyrido[1,2-c][1,3]benzoxazine-4-one (17); and
11-Hydroxy-9-(3-methyl-2-octyl)-1,2,3,12-tetrahydro-2,2,6-trimethyl-4H,6H-pyrido[1,2-c][1,3]benzoxazine-4-one (18)

With the methylated lactams 5-ethoxy-3,3,4,4-tetramethyl-2-pyrrolidinone (6), 6-ethoxy-4-methyl-2-piperidinone (15) and 4,4-dimethyl-6-ethoxy-2-piperidone (16), in the two-step procedure outlined above, respectively, in Examples 5 and 1, for the preparation of compounds (7) and (11), there were obtained respectively, compound (8) m.p. 160°–162°, compound (17), m.p. 192°–193°, and compound (18), m.p. 178°–180°.

Compound (8):
Analysis Calcd. for: $C_{25}H_{39}NO_3$: C, 74.44; H, 9.79; N, 3.49 Found: C, 74.94; H, 9.77; N, 3.25

Compound (17):
Analysis Calcd. for: $C_{23}H_{35}NO_3$: C, 73.96; H, 9.44; N, 3.75 Found: C, 73.62; H, 9.41; N, 3.64

Compound (18)
Analysis Calcd. for: $C_{24}H_{37}NO_3$: C, 74.38; H, 9.62; N, 3.61 Found: C, 74.62; H, 9.82; N, 3.32

EXAMPLE 9

Preparation of 11-Hydroxy-9-(3-methyl-2-octyl)-1,2,3,12-tetrahydro-1,3,6-trimethyl-4H,6H-pyrido[1,2-c][1,3]benzoxazine-4-one (21)

Ethoxylactam (19), as described in the procedure of Example 1, above, for the preparation of compound (11), was condensed, with 5-(3-methyl-2-octyl)-resorcinol (2) to give a 61% yield of 3,5-dimethyl-6-[2,6-dihydroxy-4-(3-methyl-2-octyl)phenyl]-2-piperidone (20) as a crystalline solid, m.p. 245°–247° (from $CH_3CN$—$CH_3OH$). The piperidone (20) was then treated with acetaldehyde to produce a 60% yield of compound (21) which was purified by column chromatography on silica gel using gradient elution ($CHCl \rightarrow$ 2% $CH_3OH$—$CHCl_3$) and was isolated as a colorless glass containing one molecule of methanol of solvation. It was essentially pure as indicated by tlc (10% $CH_3OH$—$CHCl_3$) and elemental analysis.

Analysis Calcd. for: $C_{24}H_{37}NO_3 \cdot CH_3OH$: C, 71.56; H, 9.85; N, 3.34. Found: C, 71.64; H, 9.90; N, 3.20.

EXAMPLE 10

Pharmacological Tests

There were several tests carried out with compound (11) and the results of the tests are provided below. The results for each of the tests in the use of compound (11) is compared with those of control compounds.

TEST I

Effect On Spontaneous Motor Activity In Rats

In this test, the rat motor activity tests were carried out according to known procedure. The effect on the motor activity in rats was compared between compound (11) and the untreated rat (control).

| Oral Dose, mg/kg | % Decreased Activity Over Control |
|---|---|
| 5 | 30 |
| 10 | 51 |
| 20 | 41 |
| 40 | 69 |

TEST II

Antagonism of Amphetamine Induced Increased Motor Activity in Rats

The usual procedure was used in this test and the comparison between compound (11) and the untreated rat control.

| Oral Dose, mg/kg | % Decreased Activity Over Control |
|---|---|
| 10 | 15 |
| 20 | 45 |
| 40 | 36 |
| 80 | 57 |

TEST III

Rat Sidman Avoidance Test

In the Rat Sidman Avoidance test, a decrease in rate and increase in the number of shocks tanken was noted at all doses, with the effects shown at all doses. In the results shown below there is a percentage shown from the control data. In all cases, the drug treatment was at zero time (i.e., no pretreatment).

TABLE 1

| Compound (11) in Sidman Avoidance Test | | |
|---|---|---|
| Dose | Responses (Rate) | Shocks |
| 5 mg./kg. (n=3) | −14% | +126% |
| 20 mg./kg. (n=2) | −32% | +384% |
| 80 mg./kg. (n=3) | −13% | + 26% |

As shown by the results of the test, compound (11) by oral administration, produced 35% to 55% reduction in amphetamine induced hyper-activity in rats at doses of 20 to 80 mg./kg. This was in contrast to chlorpromazine which inhibited 80 to 90% of this activity at 10 to 20 mg./kg. oral doses. At oral doses of 10 to 40 mg./kg., compound (11) reduced the spontaneous motor activity in rates by 40 to 60 percent. Compound (18) was similarly effective at doses of 20 to 80 mg./kg. By comparison, valium was 65 to 80 percent effective at dosages of 10 to 40 mg./kg., and $\Delta^9$-tetrahydrocannabinol was 40 to 60 percent effective at 5 to 20 mg./kg. orally.

The present compound can be administered orally or by injection. For the latter, solutions or suspensions may be prepared by slurrying 1% to 10% of the compound in water containing 0.1 to 2.0 percent of carboxymethyl-cellulose. Suspensions may also be prepared by using 0.05 to 0.5 percent trangacanth solutions. For oral administration, tablets. pills or capsules are easily prepared. Tablets may be prepared to contain between 5 and 25 mg. of the active material together with the usual tableting adjuvants, e.g., coloring agents, flavoring agents, diluents, lubricants, carriers and, if desired, dispersing agents or release retardants. The compound may also be combined with other active compounds such as transquilizers.

We claim:

1. A compound of the formula

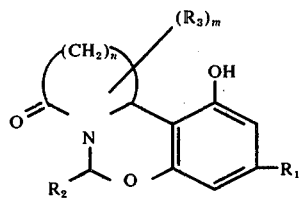

wherein $n = 2$ or 3; $R_1$ is $C_3$–$C_{20}$ alkyl or aralkyl; $R_2$ is loweralkyl or phenyl; and $R_3$ is H or replaces the hydrogens in $(CH_2)_n$ with $CH_3$; and $m$ is 1, 2 or 4.

2. The compound of claim 1, wherein $n$ is 2, $R_1$ is 3-methyl-2-octyl, $R_2$ is methyl, and $R_3$ is hydrogen.

3. The compound of claim 1 wherein $n$ is 2, $R_1$ is 3-methyl-2-octyl, $R_2$ is methyl, and $R_3$ is $CH_3$ and $m$ is 4.

4. The compound of claim 1, wherein $n$ is 3, $R_1$ is 3-methyl-2-octyl, $R_2$ is methyl, and $R_3$ is hydrogen.

5. The compound of claim 1, wherein $n$ is 3, $R_1$ is 5-(4-fluorophenyl-2-pentyl), $R_2$ is methyl, and $R_3$ is H.

6. The compound of claim 1 wherein $n$ is 3, $R_1$ is 3-methyl-2-octyl, $R_2$ is $n$-$C_3H_7$, and $R_3$ is H.

7. The compound of claim 1 wherein $n$ is 3, $R_1$ is $C_9H_{11}$, $R_2$ is phenyl, and $R_3$ is H.

8. The compound of claim 1, wherein $n$ is 3, $R_1$ is $C_9H_{19}$, $R_2$ is methyl, and $R_3$ is methyl.

9. The compound of claim 1, wherein $n$ is 3, $R_1$ is $C_9H_{19}$, $R_2$ is methyl, and $R_3$ is $CH_3$ and $m$ is 2.

10. The compound of claim 1, wherein $n$ is 3, $R_1$ is $C_9H_{19}$, $R_2$ is methyl, and $R_3$ is $CH_3$ and $m$ is 2.

11. The compound of claim 1, 11-hydroxy-6-methyl-9-(3-methyl-2-octyl)-1,2,3,12-tetrahydro-4H,6H-pyrido[1,2-c] [1,3]benzoxazine-4-one.

12. The compound of claim 1, 11-hydroxy-9-(3-methyl-2-octyl)-1,2,3,12-tetrahydro-1,3,6-trimethyl-4H,6H-pyrido[1,2-c] [1,3]benzoxazine-4-one.

13. The compound of claim 1, 11-hydroxy-9(3-methyl-2-octyl)-1,2,3,12-tetrahydro-2,2,6-trimethyl-4H,6H-pyrido [1,2,-c] [1,3]benzozanine-4-one.

* * * * *